(12) United States Patent
Merli et al.

(10) Patent No.: US 7,482,489 B2
(45) Date of Patent: Jan. 27, 2009

(54) ENANTIOMERICALLY PURE (R)-ALBUTEROL DIBENZOYLTARTRATE AND PROTECTED ANALOGS THEREOF

(75) Inventors: Valeriano Merli, Lecco (IT); Silvia Mantovani, Lendinara (IT); Stefano Bianchi, Como (IT); Paola Daverio, Milan (IT)

(73) Assignee: Teva Pharmaceutical Fine Chemicals S.r.l., Bulciago (LC) (IT)

( * ) Notice: Subject to any disclaimer, the term of this patent is extended or adjusted under 35 U.S.C. 154(b) by 453 days.

(21) Appl. No.: 11/133,721

(22) Filed: May 20, 2005

(65) Prior Publication Data

US 2005/0261368 A1 Nov. 24, 2005

Related U.S. Application Data

(60) Provisional application No. 60/573,025, filed on May 20, 2004, provisional application No. 60/577,979, filed on Jun. 7, 2004, provisional application No. 60/646,803, filed on Jan. 25, 2005, provisional application No. 60/577,819, filed on Jun. 7, 2004, provisional application No. 60/583,777, filed on Jun. 28, 2004, provisional application No. 60/583,642, filed on Jun. 28, 2004, provisional application No. 60/587,673, filed on Jul. 13, 2004, provisional application No. 60/632,625, filed on Dec. 2, 2004.

(51) Int. Cl.
*C07C 215/30* (2006.01)
*A61K 31/137* (2006.01)
*A61P 11/06* (2006.01)
*A61P 11/08* (2006.01)

(52) U.S. Cl. .................. 564/305; 564/346; 514/646

(58) Field of Classification Search ............... 564/346, 564/305; 514/646

See application file for complete search history.

(56) References Cited

U.S. PATENT DOCUMENTS

| 5,399,765 A | 3/1995 | Gao et al. |
| 5,442,118 A | 8/1995 | Gao et al. |
| 5,545,745 A | 8/1996 | Gao et al. |

FOREIGN PATENT DOCUMENTS

| CN | 1273966 A | 11/2000 |
| CN | 1382685 | 12/2002 |
| GB | 1298494 | 12/1972 |
| WO | WO 95/32178 | 11/1995 |
| WO | WO 99/42460 | 8/1999 |
| WO | WO 02/48090 A1 | 6/2002 |

OTHER PUBLICATIONS

Anonymous, (IP.com, 2004, 4(8), 9 (No. IPCOM000029577D).*
Handley, D.A., et al., "Levalbuterol hydrochloride", Exp. Opin. Invest. Drugs, 1998, 7(12), pp. 2027-2041.
Halabi, A., et al., "Validation of a chiral HPLC assay for (R)-salbutamol sulfate", Journal of Pharmaceutical and Biomedical Analysis, 2004, 34, pp. 45-51,.
Ferrayoli, C.G., et al., "Resolution of Racemic Albuterol Via Diastereomeric Salts Formation with Di-p-Toluoyl-D-Tartaric Acid", Enantiomer, 2000, 5, pp. 289-291.
Caira, M.R., "Crystalline Polymorphism of Organic Compounds", Topics in Current Chemistry, 1998, 198, pp. 163-208.
"Briefing: Levalbuterol Hydrochloride; Levalbuterol Inhalation Solution" 2006 USPC, Inc. 33(1) In-Process Revision: Levalbuterol Hydrochloride, downloaded 2006, http://www.usppf.com/pf/pub/data/v331/MON_IPR_331_m44602.xml, pp. 1-6.

* cited by examiner

*Primary Examiner*—Brenda Coleman
*Assistant Examiner*—Susanna Moore
(74) *Attorney, Agent, or Firm*—Kenyon & Kenyon LLP

(57) ABSTRACT

Provided are processes for the preparation of (R)-SLB.D-DBTA salt and levalbuterol hydrochloride. Also provided are levalbuterol hydrochloride degradation products and processes for preparing them. Pharmaceutical compositions comprising at least one levalbuterol hydrochloride of the invention and at least one pharmaceutically-acceptable excipient are also provided.

2 Claims, No Drawings

ENANTIOMERICALLY PURE (R)-ALBUTEROL DIBENZOYLTARTRATE AND PROTECTED ANALOGS THEREOF

CROSS-REFERENCE TO RELATED APPLICATIONS

This application claims the benefits of U.S. Provisional Patent Application Nos. 60/573,025, filed May 20, 2004, 60/577,979, filed Jun. 7, 2004, 60/646,803, filed Jan. 25, 2005, 60/577,819, filed Jun. 7, 2004, 60/583,777, filed Jun. 28, 2004, 60/583,642, filed Jun. 28, 2004, 60/587,673, filed Jul. 13, 2004 and 60/632,625, filed Dec. 2, 2004, the contents of all of which are incorporated herein by reference.

FIELD OF THE INVENTION

The invention encompasses processes for the preparation of (R)-SLB.D-DBTA salt, and levalbuterol hydrochloride. The invention also encompasses levalbuterol hydrochloride degradation products and processes for preparing them. Also provided are pharmaceutical compositions comprising at least one levalbuterol hydrochloride of the invention and at least one pharmaceutically-acceptable excipient.

BACKGROUND OF THE INVENTION

Activation of $\beta_2$-adrenergic receptors on airway smooth muscle leads to the activation of adenylcyclase and to an increase in the intracellular concentration of cyclic-3',5'-adenosine monophosphate (cyclic AMP). This increase in cyclic AMP leads to the activation of protein kinase A, which inhibits the phosphorylation of myosin and lowers intracellular ionic calcium concentrations, resulting in relaxation. Levalbuterol relaxes the smooth muscles of the airways, from the trachea to the terminal bronchioles. Levalbuterol acts as a functional antagonist to relax the airway irrespective of the spasmogen involved thus protecting against all bronchoconstrictor challenges. Increased cyclic AMP concentrations are also associated with the inhibition of release of mediators from mast cells in the airway. The chemical name for levalbuterol HCl is (R)-$\alpha^1$-[[(1,1-dimethylethyl)amino]methyl]-4-hydroxy-1,3-benzenedimethanol hydrochloride.

Levalbuterol HCl has been synthesized using a variety of synthetic schemes. For example, Great Britain patent No. 1298494 discloses synthesizing levalbuterol first by crystallizing the alkyl acetate of the 4-carboxylate derivative (Formula 1) using ditolyltartaric acid and isolating the selected crystalline fraction. Thereafter, the crystal undergoes debenzylation deprotection, followed by ester reduction to yield levalbuterol.

Formula 1

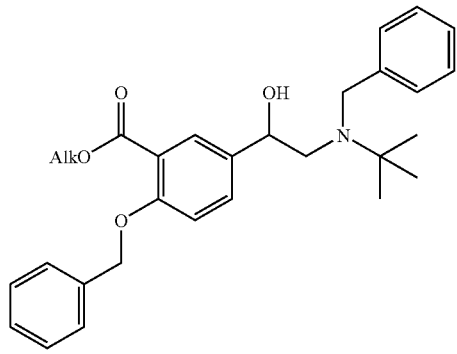

Several patents report synthetic routes using enantiomeric separation, however, the synthetic routes result in low yields of the enantiomerically pure product. Optically pure levalbuterol was synthesized by the borane-methylsulfide reduction of the enantiomerically pure precursor (Formula 2) as described in U.S. Pat. No. 5,399,765. The reaction dissolved a mixture of enantiomers of methyl 5-[2-[(1,1-dimethylethyl) amino]-1-hydroxyethyl]-2-hydroxybenzoate and a chiral acid selected from (−)-di-toluoyl-L-tartaric acid and (+)-di-toluoyl-D-tartaric acid in methanol, upon cooling one stereoisomer crystallized, which was separated, and recrystallized as a diastereomer from methanol, the diastereomer was separated, treated with base, and upon reduction formed optically active levalbuterol.

Formula 2

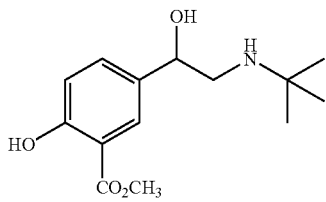

U.S. Pat. No. 5,442,118 discloses the synthesis of optically pure (R) or (S) levalbuterol by the asymmetric reduction of α-iminoketones precursors. In particular, levalbuterol is synthesized by the reduction with borane-methylsulfide complex in the presence of chiral oxazaborolidines as catalysts.

During the synthesis of levalbuterol, D-dibenzoyltartaric acid (D-DBTA) or D-ditoluoyltartaric acid (D-DTTA) have been used for enantiomeric separation. Typically, during the enantiomeric separation, at least one of the alcohol, ester, or amine functional groups on levalbuterol is protected. The protecting group is typically a benzyl group, which after separation is removed to yield levalbuterol. See U.S. Pat. No. 5,545,745 and WO 95/32178.

The prior art has separated levalbuterol enantiomers using 4-benzyl levalbuterol. See WO 02/48090. The synthesis uses tartaric acid for enantiomeric separation and once the (L) tartaric acid salt is formed and one enantiomer separated, then the salt is debenzylated to yield either the (R) or (S) isomer of salbutamol as a sulphate salt.

Other publications have separated levalbuterol derivatives, such as WO 99/42460, by forming the ketal derivative of levalbuterol prior to enantiomeric separation with an enantiomer of di-O-benzoyl tartaric acid or di-O-(p-toluoyl)-tartaric acid. Thus, after enantiomeric separation of the ketal, the derivative is hydrolyzed to yield the desired levalbuterol enantiomer. The process continuously recycles the undesired enantiomer in the derivatize, resolve, and hydrolyze cycle to further enhance the overall yield of the desired enantiomer.

In Chinese patent No. 1,273,966, enantiomers of racemic salbutamol are separated using tartaric acid, D-DBTA, D-DTTA, or a mixture thereof as a resolving agent. In the examples provided, the ratios of reaction solvent to salbutamol were at least about 14 ml/g. Levalbuterol hydrochloride is isolated by acid-base work-up or by solid-solid transformation in acetone. In one example, the salt of (R)-levalbuterol D-dibenzoyltartaric acid is treated with potassium carbonate in water and an organic solvent, such as ethylacetate. After phase separation and extraction of the aqueous layer, the organic layer is dried and the levalbuterol free base is precipitated overnight. Levalbuterol HCl is synthesized by acid displacement from (R)-levalbuterol D-dibenzoyltartaric acid salt suspended in acetone and the addition of an ether solution of HCl.

Despite the many attempts of the prior art to synthesize enantiomerically pure levalbuterol, novel synthetic processes of levalbuterol are still needed to reduce the steps necessary for synthesis while maximizing synthetic yield without sacrificing compound purity.

SUMMARY OF THE INVENTION

The invention encompasses processes for preparing (R)-SLB.D-DBTA comprising preparing a mixture of racemic salbutamol in a first $C_1$-$C_4$ alcohol; adding D-dibenzoyltartaric acid to the mixture; crystallizing and isolating crude (R)-SLB.D-DBTA; and recrystallizing the crude (R)-SLB.D-DBTA in a second $C_1$-$C_4$ alcohol to obtain the (R)-SLB.D-DBTA, wherein the first or second alcohol is present in an amount of about 2 ml/g to about 7.5 ml/g of the salbutamol. In one embodiment, the first or second alcohol is methanol. The crystallizing step is performed by seeding with (R)-SLB.D-DBTA. In the process, the D-dibenzoyltartaric acid is present in an amount of about 0.5 mol to about 1.3 mol equivalents of the salbutamol.

Another embodiment of the invention encompasses enantiomerically pure (R)-SLB.D-DBTA salt having an enantiomeric excess of at least about 99.8%.

Yet another embodiment of the invention encompasses processes for preparing levalbuterol hydrochloride comprising preparing a first slurry of (R)-SLB.D-DBTA in a first solvent; adding hydrochloric acid to the first slurry to form crude levalbuterol hydrochloride; isolating the crude levalbuterol hydrochloride; preparing a second slurry of the crude levalbuterol hydrochloride in a second solvent; and isolating the levalbuterol hydrochloride. In the process, the first or second solvent is at least one of $C_3$-$C_{10}$ ester, $C_3$-$C_{10}$ ketone, $C_3$-$C_{10}$ ether, $C_1$-$C_4$ alcohol, $C_6$-$C_{12}$ aromatic hydrocarbon, tetrahydrofuran, dimethylcarbonate, dimethylsulfoxide, dimethylformamide, dichloromethane, or acetonitrile. In particular, the first solvent is at least one of ethylacetate, acetone, tetrahydrofuran, dimethylcarbonate, acetonitrile, toluene, xylene, methanol, ethanol, isopropanol, dimethylsulfoxide, or dimethylformamide. The second solvent is at least one of methanol, ethanol, isopropanol, ethylacetate, butyl acetate, DMF, acetone, toluene, isopropyl ether, diethyl ether, methyl tert butyl ether, dichloromethane, or acetonitrile. Optionally, the second solvent further comprises water, for example, acetone and water. In one embodiment, the hydrochloric acid is present in an amount of about 1 mol to about 1.3 mol equivalents of the (R)-SLB.D-DBTA. The slurry may be cooled at a temperature of about −20° C. to about 10° C. In the process, the HCl may be added as a solution or a gas.

Another embodiment of the process encompasses where the first or second solvent is at least one $C_3$-$C_6$ ester or a mixture of at least one $C_1$-$C_4$ alcohol and $C_3$-$C_6$ ester. Preferably, the alcohol is methanol and the ester is ethylacetate. Also, the first or second solvent has an alcohol to ester ratio of about 15:85 by volume.

Yet another embodiment of the invention encompasses levalbuterol hydrochloride characterized by at least one of an enantiomeric excess of at least about 99.8%; having less than about 1700 ppm of residual $C_1$-$C_4$ alcohol; or having a pH of at least about 4.3 in 1% aqueous solution at room temperature. Preferably, the residual alcohol is methanol. In one embodiment, the pH is about 4.5 to about 7.

Yet another embodiment of the invention encompasses levalbuterol hydrochloride characterized by at least one of having less than about 0.15% by area HPLC of total at least one of Compound A, Compound B, or Compound C; having less than about 0.10% by area HPLC of total unknown impurities; or having less than about 0.25% by area HPLC of total impurities including Compound A, Compound B, and Compound C, after being stored for three months at 40° C. and 75% relative humidity.

Another embodiment of the invention encompasses N-(tert-butyl)-2-methoxy-2-(4-hydroxy-3-(hydroxymethyl) phen-1-yl-ethanamine, Compound B, having the following structure:

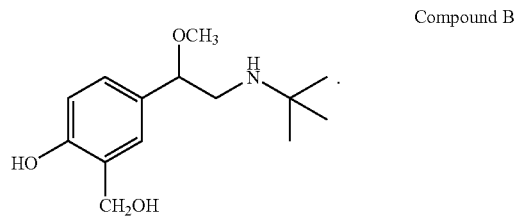

Compound B

Another embodiment of the invention encompasses N-(tert-butyl)-2-methoxy-2-(4-hydroxy-3-(methoxymethyl) phen-1-yl)-ethanamine, or Compound C having the following structure:

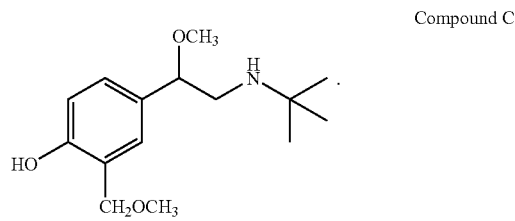

Compound C

Yet another embodiment of the invention encompasses pharmaceutical compositions comprising a therapeutically effective amount of the levalbuterol hydrochloride of the invention and at least one pharmaceutically-acceptable excipient.

DETAILED DESCRIPTION OF THE INVENTION

The invention encompasses enantiomerically pure (R)-salbutamol.D-dibenzoyltartrate ("(R)-SLB.D-DBTA") salt, levalbuterol hydrochloride in enantiomerically pure form, and processes for their preparation. Typically, the processes require fewer steps and result in higher yields and/or optical purity than conventional processes. The invention also encompasses polymorphs of levalbuterol and compounds synthesized during the preparation of levalbuterol.

In particular, the invention encompasses processes for separating racemic salbutamol enantiomers using D-dibenzoyltartrate ("D-DBTA") as a resolving agent. The processes do not require the protection of the alcohol or amine functional groups and require significantly less solvent than conventional processes to prepare enantiomerically pure (R)-SLB.D-DBTA. The use of less solvent is advantageous especially in industrial scale production due to cost, efficiency, and pollution considerations. Furthermore, the processes yield after two crystallization steps (R)-SLB.D-DBTA salt in 40-43% yield and an enantiomeric excess of at least about 99.8%. Enantiomerically pure (R)-SLB.D-DBTA salt is useful for preparing levalbuterol hydrochloride with high optical purity. Not to be limited by theory, it is believed that the (R)-SLB.D-DBTA salt converts to levalbuterol hydrochloride in a solid-solid transformation.

The process for preparing (R)-SLB.D-DBTA salt comprises preparing a mixture of racemic salbutamol in a first $C_1$-$C_4$ alcohol; adding D-dibenzoyltartaric acid to the mixture; crystallizing and isolating crude (R)-SLB.D-DBTA salt; and recrystallizing the crude (R)-SLB.D-DBTA salt in a second $C_1$-$C_4$ alcohol to obtain the (R)-SLB.D-DBTA salt.

The first alcohol is present in any amount sufficient to dissolve the racemic salbutamol and D-dibenzoyltartaric acid at reflux. Preferably, the alcohol is present in an amount of about 2 ml/g to about 7.5 ml/g of the racemic salbutamol, more preferably about 2 ml/g to about 5 ml/g, and most preferably about 4 ml/g to about 5 ml/g. $C_1$-$C_4$ Alcohols include, but are not limited to, at least one of methanol, ethanol, propanol, isopropanol, butanol, isobutanol, or tert-butanol. The preferred alcohol is methanol.

The D-dibenzoyltartaric acid may be present in any amount sufficient to form the (R)-SLB.D-DBTA salt. Preferably, the D-dibenzoyltartaric acid is present in an amount of about 0.5 mol to about 1.3 mol equivalents of the salbutamol, and more preferably about 1 mol equivalent.

The mixture of racemic salbutamol and a first alcohol may be heated to form a solution, preferably at a temperature of at least about 50° C. More preferably, the mixture is heated at about reflux temperature. Depending on the solvent used, the solution may be heated at other suitable temperatures as long as the racemic salbutamol and D-dibenzoyltartaric acid are sufficiently dissolved. For example, where the reaction solvent is methanol, the mixture is preferably heated at about 60° C. to about 65° C.

The crude (R)-SLB.D-DBTA may be crystallized by methods such as seeding. Seeding may be carried out as soon as the solution is cool enough not to dissolve the seeding material. Preferably, the solution is cooled before seeding at a temperature below reflux, and more preferably at a temperature of about 50° C.

Preferably, the solution is seeded with (R)-SLB.D-DBTA having an enantiomeric excess of at least about 99%. After seeding, the solution is cooled at a temperature that permits crystal formation without causing the solution to freeze. The solution may be cooled at any rate that facilitates formation of the (R)-SLB.D-DBTA salt. Preferably, the solution is cooled at a temperature of about −20° C. to about 10° C., more preferably at about −10° C. to about 10° C., and most preferably at about −5° C. The solution may be cooled to a preferred temperature immediately after seeding, or cooled within a period of about 15 hours. The crude (R)-SLB.D-DBTA salt may be isolated by filtration and washed with additional solvent prior to recrystallization.

The second $C_1$-$C_4$ alcohol used for recrystallization can be the same as the alcohol used during the reaction of salbutamol and D-dibenzoyltartaric acid, or it can be different. The preferred alcohol for recrystallization is methanol. The second alcohol is present in any amount sufficient to crystallize (R)-SLB.D-DBTA salt. Preferably, the alcohol is present in an amount of about 2 ml/g to about 5 ml/g of the racemic salbutamol, and more preferably, in about 3 ml/g to about 4 ml/g.

The second alcohol is heated, preferably at reflux, to dissolve the crude (R)-SLB.D-DBTA salt and form a solution. The solution may be treated with charcoal and filtered, after which the solution is further heated, followed by cooling, to precipitate the enantiomerically pure (R)-SLB.D-DBTA salt. The precipitated (R)-SLB.D-DBTA salt is preferably isolated by filtration and washed with additional solvent.

The invention encompasses enantiomerically pure (R)-SLB.D-DBTA. As used herein, "enantiomerically pure" refers to an enantiomeric excess of at least about 99.8%. Enantiomeric excess, as well as chemical purity, are determined by area percent HPLC.

The invention also encompasses processes for preparing levalbuterol hydrochloride. The process comprises preparing a first slurry of (R)-SLB.D-DBTA in a first solvent; adding hydrochloric acid to the first slurry to form crude levalbuterol hydrochloride, and isolating crude levalbuterol hydrochloride. Optionally, the process may further comprise preparing a second slurry of the crude levalbuterol hydrochloride in a second solvent; and isolating the levalbuterol hydrochloride.

A suitable first solvent is one in which levalbuterol hydrochloride is insoluble and DBTA is soluble. The first solvent includes, but is not limited to, at least one linear or branched $C_3$-$C_6$ ester, $C_3$-$C_{10}$ ketone, $C_3$-$C_{10}$ ether, $C_1$-$C_4$ alcohol, $C_6$-$C_{12}$ aromatic hydrocarbon, dimethylcarbonate, acetonitrile, dimethylsulfoxide, or dimethylformamide. Preferably, the first solvent includes, but is not limited to, at least one of ethylacetate, acetone, tetrahydrofuran, dimethylcarbonate, acetonitrile, toluene, xylene, methanol, ethanol, isopropanol, dimethylsulfoxide, or dimethylformamide. More preferably, the first solvent is at least one of ethylacetate, methanol, acetonitrile, or dimethylformamide. When two solvents are used, the ratio of solvents is preferably about 90 to about 10 by volume, or about 95 to about 5 by volume.

Before addition of the hydrochloric acid, the first slurry may be cooled, preferably at a temperature of about 10° C. to about −20° C., and more preferably at about 0° C. to about 2° C. The reaction may be carried out at temperatures of about −10° C. to about 40° C.

The HCl may be added as a solution or a gas. For example, methods for adding HCl include, but are not limited to, adding aqueous HCl (37%), HCl gas, HCl in at least one $C_1$-$C_4$ alcohol, or HCl in dimethylformamide. Typically, when present as a solution in an alcohol, the HCl is present in 5% concentration. Typically, HCl is added in an amount of about 1 mol to about 1.3 mol equivalents of the (R)-SLB.D-DBTA, and preferably about 1.2 mol equivalent.

The crude levalbuterol hydrochloride is isolated by filtration and preferably washed with additional portions of the first solvent prior to preparation of the second slurry.

When present, the second solvent for preparing the second slurry includes, but is not limited to, at least one linear or branched $C_3$-$C_6$ ester, $C_3$-$C_{10}$ ketone, $C_3$-$C_{10}$ ether, $C_1$-$C_4$ alcohol, $C_6$-$C_{12}$ aromatic hydrocarbon, dimethylcarbonate, dimethylformamide, dimethylsulfoxide, dichloromethane, or acetonitrile. Preferably, the second solvent is at least one of methanol, ethanol, isopropanol, ethylacetate, butyl acetate, DMF, acetone, toluene, isopropyl ether, diethyl ether, methyl tert butyl ether, dichloromethane, or acetonitrile. Water may be added to the second solvent, preferably with acetone.

The slurry may be carried out at a temperature of about −10° C. to about the reflux temperature of the second solvent. The second slurry may be carried out at room temperature, or about 20° C. to about 25° C. The levalbuterol hydrochloride is preferably isolated by filtration and washed with additional portions of the second solvent. Optionally, the levalbuterol hydrochloride is dried, such as at room temperature under reduced pressure.

In a preferred embodiment, the first and second solvents may be an ester, an alcohol, or a combination thereof. For example, the first or second solvent is a $C_3$-$C_6$ ester or a mixture of a $C_1$-$C_4$ alcohol and a $C_3$-$C_6$ ester. $C_3$-$C_6$ Esters include, but are not limited to, at least one of methylacetate, ethylacetate, isopropyl acetate, butyl acetate, or isobutyl acetate. The preferred ester is ethylacetate. $C_1$-$C_4$ Alcohols include, but are not limited to, at least one of methanol, ethanol, propanol, or butanol. Methanol is the preferred alcohol. When the first solvent is a mixture, the alcohol to ester ratio is preferably about 15:85 by volume, and more preferably about 5:95 by volume. When the second solvent is a mixture, the alcohol to ester ratio is preferably about 15:85 by volume, and more preferably about 1:9 by volume.

The above described process may prepare enantiomerically pure levalbuterol hydrochloride by the use of enantiomerically pure (R)-SLB.D-DBTA as a starting material. For example, the levalbuterol hydrochloride is prepared by forming a first slurry of enantiomerically pure (R)-SLB.D-DBTA in a first solvent.

The invention also encompasses levalbuterol hydrochloride degradation products useful for identifying impurities within an levalbuterol hydrochloride sample. Isolated levalbuterol hydrochloride degradation products may be used to quantify an impurity content of a levalbuterol hydrochloride sample. A sample of levalbuterol hydrochloride may be spiked with a known amount of the degradation product and analyzed by HPLC to identify the impurities. An impurity level can be determined by comparing the area percent by HPLC of a known impurity with the area percent of the corresponding standard impurity injected in a known amount within linearity range. When levalbuterol is prepared with methanol, benzylic and secondary alcoholic functional groups undergo etherification to produce the following impurities:

Compound A

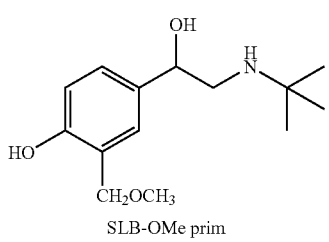

SLB-OMe prim

Compound B

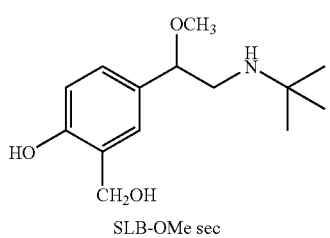

SLB-OMe sec

Compound C

SLB-di-OMe

One degradation product is N-(tert-butyl)-2-methoxy-2-(4-hydroxy-3-(hydroxymethyl)phen-1-yl-ethanamine, or Compound B:

Compound B

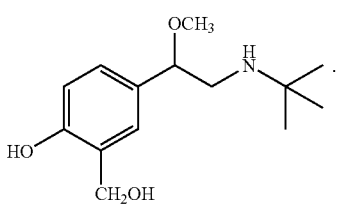

Another degradation product is N-(tert-butyl)-2-methoxy-2-(4-hydroxy-3-(methoxymethyl)phen-1-yl)-ethanamine, or Compound C:

Compound C

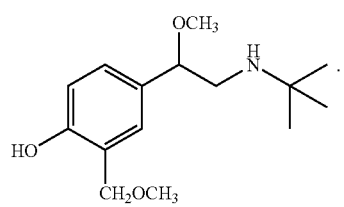

The invention further encompasses levalbuterol hydrochloride having low residual alcohol content and/or a stabilizing pH in aqueous solution. It has been found that residual alcohol content and/or pH affect the stability of levalbuterol over time.

The levalbuterol hydrochloride made by the processes described above typically has less than about 1700 ppm of residual $C_1$-$C_4$ alcohol. Preferably, the levalbuterol hydrochloride has 1600 ppm or less residual $C_1$-$C_4$ alcohol. Preferably, the residual alcohol is methanol. Table 1 exemplifies the effect of the first solvent used during the transformation of (R)-SLB.D-DBTA in hydrochloride on the residual alcohol content of the final product. For the examples of Table 1, the second solvent is a mixture of methanol:ethylacetate at 1:9 by volume.

TABLE 1

| | First solvent and residual methanol content. | |
|---|---|---|
| Example | First solvent (volume ratio) | Residual MeOH (ppm) |
| 1 | AcOEt—MeOH 85-15 | 5500 |
| 2 | AcOEt—MeOH 90-10 | 5300 |
| 3 | AcOEt—MeOH 90-10 | 7000 |
| 4 | AcOEt—MeOH 90-10 | 6700 |
| 5 | AcOEt—MeOH 92.5-7.5 | 1950 |
| 6 | AcOEt—MeOH 95-5 | 1300 |
| 7 | AcOEt—MeOH 95-5 | 1700 |
| 8 | AcOEt—MeOH 95-5 | 1470 |
| 9 | AcOEt—MeOH 95-5 | 1500 |
| 10 | AcOEt—MeOH 95-5 | 1160 |
| 11 | AcOEt—MeOH 95-5 | 1270 |
| 12 | AcOEt | 700 |
| 13 | AcOEt | 878 |
| 14 | AcOEt | 640 |
| 15 | AcOEt | 620 |

Table 1 illustrates that the alcohol present in the first solvent has an effect on residual alcohol in the product. For example, if the ratio of ester to alcohol is 95:5 or higher, then the levalbuterol hydrochloride with a residual alcohol content has less than about 1700 ppm of residual alcohol.

In another embodiment, the levalbuterol hydrochloride has a pH of at least about 4.3 in 1% aqueous solution at room temperature. Preferably, the pH is about 4.5 to about 7. The effect of residual alcohol content and pH on the stability of levalbuterol hydrochloride when stored at 70° C. is exemplified in Table 2. Preferably, the levalbuterol hydrochloride of the invention has less than about 1600 ppm or less of residual $C_1$-$C_4$ alcohol and a pH of at least about 4.3 in 1% aqueous solution at room temperature.

TABLE 2

Stability of levalbuterol hydrochloride at 70° C.

| Sample | Time | LVB[a] | Compound A | Compound B | Compound C | Total Unknown Impurities | pH[b] | MeOH (ppm) |
|---|---|---|---|---|---|---|---|---|
| White solid | T = 0 | 99.9% | 0.05% | 0.02% | n.d. | 0.04% | 4.41 | 300 |
| White solid | 1 week | 99.8% | 0.06% | 0.02% | n.d. | 0.04% | | |
| White solid | T = 0 | 99.8% | 0.03% | 0.02% | n.d. | 0.10% | 5.30 | 1500 |
| White solid | 1 week | 99.7% | 0.10% | 0.06% | 0.03% | 0.07% | | |
| White solid[c] | T = 0 | 99.4% | 0.24% | 0.18% | 0.15% | n.d. | 3.97 | 3420 |
| Pale yellow solid | 1 week | 97.1% | 0.72% | 0.26% | 0.18% | 1.21% | | |
| White solid | T = 0 | 99.8% | 0.04% | 0.05% | n.d. | 0.06% | 3.70 | 700 |
| Yellow solid | 1 week | 98.9% | 0.22% | 0.06% | 0.05% | 0.45% | | |
| White solid | T = 0 | 99.8% | 0.02% | 0.01% | n.d. | 0.12% | 3.50 | 878 |
| Yellow solid | 1 week | 93.1% | 0.27% | 0.08% | 0.07% | 4.72% | | |

[a]Levalbuterol hydrochloride.
[b]Measured at 22-23° C. in 1% aqueous solution.
[c]Made according to Example 21.

Table 2 demonstrates that pH and/or residual alcohol content affect the degradation of levalbuterol hydrochloride and/or the presence of degradation products Compounds A, B, C, or other impurities. At similar pH values, samples with greater residual alcohol content resulted in higher levalbuterol hydrochloride degradation. At lower pH values, greater levalbuterol hydrochloride degradation occurred. In addition, it was observed that samples with high residual methanol content or low pH values after storage for 1 week at 70° C. became yellow, whereas samples with low residual methanol content and a pH of at least about 4.3 remained as white solids. The effect of storage temperature on the stability of levalbuterol hydrochloride is illustrated in Table 3.

TABLE 3

Stability of levalbuterol hydrochloride at 40-45° C., 50-55° C., and 25° C.

| Sample | Time | T (° C.) | LVB | Compound B | Compound A | Total Unknown Impurities | MeOH (ppm) |
|---|---|---|---|---|---|---|---|
| 1 | T = 0 | 20° C. | 99.84% | 0.035% | 0.028% | 0.097% | 6700 |
| 2 | 20 hrs | 40-45° C. | 99.30% | 0.30% | 0.11% | 0.29% | — |
| 3 | 20 hrs | 55-60° C. | 98.17% | 0.45% | 0.23% | 1.15% | — |
| 4 | 32 hrs | 55-60° C. | 97.9% | 0.45% | 0.26% | 1.39% | — |
| 5 | T = 0 | 25° C. | 99.90% | 0.01% | 0.02% | 0.07% | 2090 |
| 6 | 10 days | 25° C. | 99.88% | 0.01% | 0.02% | 0.09% | — |
| 7 | 1 month | 25° C. | 99.87% | 0.02% | 0.03% | 0.08% | — |
| 8 | 2 months | 25° C. | 99.82% | 0.02% | 0.04% | 0.12% | — |

Table 3 illustrates that greater levalbuterol hydrochloride decomposition occurred at elevated storage temperatures. The invention encompasses levalbuterol hydrochloride where the amount of each of Compound A, Compound B, or Compound C after storage for three months at 40° C. and 75% relative humidity is less than about 0.15% by area HPLC. The percentage LVB, Compound B, or Compound A is relative to the total amount of sample at time=T.

In another embodiment, the levalbuterol hydrochloride has total amount of unknown impurities after storage for three months at 40° C. and 75% relative humidity of less than about 0.10% by area HPLC. The term "unknown impurities" refers to any impurity in the sample other than Compound A, Compound B, or Compound C.

The invention also encompasses levalbuterol hydrochloride where the total amount of impurities including Compound A, Compound B, and Compound C after storage for three months at 40° C. and 75% relative humidity is less than about 1% by area HPLC.

Levalbuterol hydrochloride having at least one of the impurity profiles described above preferably has less than about 1700 ppm of residual $C_1$-$C_4$ alcohol and/or a pH of at least about 4.3 in 1% aqueous solution at room temperature and/or less than 1% of impurities. Preferably, the levalbuterol hydrochloride has less than 0.5% of impurities.

The invention encompasses pharmaceutical compositions comprising at least one levalbuterol hydrochloride of the invention and at least one pharmaceutically-acceptable excipient. The pharmaceutical composition may contain a single levalbuterol hydrochloride polymorphic form, a mixture of various crystalline forms, and/or the amorphous form.

Any excipient commonly known and used widely in the art can be used in the pharmaceutical composition. The excipients included in the composition are determined primarily by the manner in which the composition is to be administered. For example, a composition to be administered in inhalant form can include a liquid carrier and/or propellant. A composition to be administered in tablet form can include a filler (e.g., lactose), a binder (e.g., carboxymethyl cellulose, gum arabic, gelatin), an adjuvant, a flavoring agent, a coloring agent, or a coating material (e.g., wax or a plasticizer). A composition to be administered in liquid form can include, for example, an emulsifying agent, a flavoring agent and/or a coloring agent.

The pharmaceutical composition comprising the levalbuterol hydrochloride can be administered by inhalation, by subcutaneous or other injection, orally, intravenously, topically, parenterally, transdermally, rectally or via an implanted reservoir containing the drug. The form in which the drug will be administered (e.g., inhalant, powder, tablet, capsule, solution, emulsion) will depend on the route by which it is administered.

If a conflict exists between a compound's nomenclature and chemical structure, the chemical structure will define the compound. While the invention is described with respect to particular examples and preferred embodiments, it is understood that the invention is not limited to these examples and embodiments. The invention as claimed therefore includes variations from the particular examples and preferred embodiments described herein, as will be apparent to one of skill in the art.

EXAMPLES

Yields were determined by mass. Chemical purity was determined by HPLC. The HPLC analysis was conducted using a column POLARIS C18-A 250 mm×4.6 mm×5.0 mm (cat n.2002-250×046) and a mobile phase. The mobile phase comprised a phosphate buffer at pH 3.00 and acetonitrile in a gradient. The eluent flow was 1.0 ml/min. The detector was set to a wavelength of 230 nm, using an HPLC Hewlett Packard VWD detector HP 1100, as a detector.

Enantiomeric excess was determined by HPLC using a chiral column. The column and packing was a CHIREX S-indoline-carboxylic acid-R-α-naphylethylamine 250 mm×4.60 mm (Phenomenex cat. N^ 00G-3022-EO) and the diluent was a mobile phase. The mobile phase was a mixture of n-hexane:$CH_2Cl_2$:MeOH:$CF_3COOH$ (500:440:60:0.4 by volume, respectively). Each chromatogram was run for to 20 minutes. The column temperature was 25° C. and the flow rate was 1.5 ml/min. The detector was set to UV at 280 nm.

The X-Ray diffraction (XRD) analysis was conducted using an ARL X-Ray powder diffractometer (model X'TRA-030) equipped with a Peltier detector, round standard aluminum sample holder with round zero background, and quartz plate. The scanning parameters were from a range of about 2-40 degree two θ (±0.2 degrees) and a continuous scan at a rate of about 3 degrees/min. One of ordinary skill in the art understands that experimental differences may arise due to differences in instrumentation, sample preparation, or other factors.

Fourier transform infrared (FT-IR) spectroscopy was conducted using a Perkin-Elmer Spectrum 1000 Spectrometer at about 4 $cm^{-1}$ resolution with about 16 scans in the range of 4000-400 $cm^{-1}$. Samples were analyzed in KBr pellet and the instrument was calibrated using an empty cell as a background.

Differential scanning calorimetry (DSC) was conducted using a Mettler Toledo DSC $822^e$/700 with a sample weight of about 3-5 mg, a heating rate of about 10° C./min., using a 3 holed crucible, under a stream of $N_2$ at a flow rate of about 40 ml/min. The sample was scanned between a range of about 30° C. to about 250° C. at a heating rate of about 10° C./minute.

Thermal Gravimetric Analysis (TGA) was conducted using a Mettler Toledo TGA/SDTA $851^e$ using a sample weight of about 7-15 mg, a heating rate of about 10° C./min. under a $N_2$ stream at a $N_2$ flow rate of about 50 ml/min. The samples were scanned at a range between about 30° C. to about 250° C.

Example 1

Preparation of Crude (R)-SLB.D-DBTA, or (R)(−) $α^1$-[[(1,1Dimethylethyl)amino]methyl]-benzenedimethanol.(D)-Dibenzoyltartrate In a 2 L reactor equipped with a condenser, thermometer, and mechanical stirrer at 20° C. and under nitrogen, salbutamol base (200 g), D-DBTA (150 g), and methanol (900 mL) were loaded. The temperature increased from 20° C. to 32° C. to form a solution. The solution was cooled to 25° C., and a second portion of D-DBTA (150 g) was loaded. The solution was heated to 60-63° C. The solution was cooled to 50° C. and seeded with pure (R)-SLB.D-DBTA (enantiomeric excess>99%, 0.350 g). Precipitation formed, and the mixture was maintained at 50° C. for 30 min, cooled to −5° C.±2° C. in 2 hours, and maintained at the temperature for 2 hours after which a solid appeared. The solid was collected by filtration and washed with cold methanol (2×100 mL).

Crude (R)-SLB.D-DBTA was obtained as a wet solid (319.14 g). The wet product was crystallized according to the procedure described in Example 2.

Example 2

Preparation of Pure (R)-SLB.D-DBTA, or (R)(−) $β^1$-[[(1,1 Dimethylethyl)amino]methyl]-benzenedimethanol.(D)-Dibenzoyltartrate In a 1 L reactor equipped with a condenser, thermometer, and mechanical stirrer at room temperature and under nitrogen, a suspension of wet (R)-SLB.(D)-DBTA (Loss on Drying 21.7%, 319.14 g) in methanol (660 mL) was formed. The suspension was heated to light reflux (62-63° C.) until a solution formed. The solution was cooled at 60° C., and treated with charcoal (2.5 g). After 15 min at 60-62° C. the charcoal was filtered off while the solution was maintained at 60-62° C. to avoid crystallization.

The filtrate, a clear solution, was cooled at 50° C. to obtain crystals. The solution was maintained at 50° C. for 30 min, cooled to −5° C. in 2 hours, and maintained at the temperature for 3 hours. The solid was collected by filtration and washed with cold methanol (160 mL) and ethylacetate (3×160 mL) to obtain a wet solid (253.6 g). The wet solid was dried for 24 hours at 20-25° C. under vacuum to obtain pure (R)-SLB.D-DBTA (dry 213.5 g).

The crystallization yield was 87.6%. The overall yield from racemic salbutamol was 42.7%. The enantiomeric excess of pure (R)-SLB.D-DBTA was 99.8%.

Example 3

Preparation of Crude Levalbuterol Hydrochloride

In a 2 L reactor equipped with a condenser, thermometer, and mechanical stirrer at room temperature and under nitrogen, a suspension of pure (R)-SLB.D-DBTA (150 g, 0.25 mol), ethylacetate (1710 mL), and methanol (90 mL) was formed. The suspension was cooled to 0° C.±2° C., and HCl (37%, 29.44 g, 0.30 mol) was added in about 15 minutes. The temperature was maintained at 0° C.±2° C. The suspension was stirred at 0° C.±2° C. for 1 hour. The solid was collected by filtration and washed with an ethylacetate:methanol mixture (95:5, 80 mL), followed by washing with ethylacetate (2×80 mL).

The wet product (97.6 g) was slurried according to the procedure described in Example 4.

Example 4

Preparation of Pure Levalbuterol Hydrochloride

In a 2 L reactor equipped with a condenser, thermometer, and mechanical stirrer at 20° C. and under nitrogen, a suspension of wet levalbuterol hydrochloride (97.6 g), ethylacetate (440 mL) and methanol (49 mL) was formed. The suspension was stirred at 22° C.±2° C. for 4 hours. The solid was collected by filtration and washed with an ethylacetate:methanol mixture (90:10, 97 mL), and ethylacetate (2×97 mL). The product was dried at 22° C.±2° C. under vacuum (res. press. 40-45 mm Hg) for 24 hours to obtain 64.0 g (dry weight) in 92.5% yield from pure (R)-SLB.D-DBTA. The overall yield from racemic salbutamol to pure levalbuterol hydrochloride: 39.5%.

Example 5

Preparation of Crude (R)-SLB.D-DBTA, or (R)(−) α$^1$-[[(1,1 Dimethylethyl)amino]methyl]-benzene-dimethanol.(D)-Dibenzoyltartrate In a 10 L reactor equipped with a condenser, thermometer, and mechanical stirrer at 20° C. and under nitrogen, salbutamol base (800 g), D-DBTA (400 g), and methanol (3600 mL) were loaded. The temperature increased from 20° C. to 26° C. A second aliquot of D-DBTA (400 g) was loaded and the temperature increased to 31° C. A third aliquot of D-DBTA (400 g) was loaded, the temperature increased to 32° C. and a solution was obtained. The solution was heated to 60-63° C. The solution was cooled to 50° C. and seeded with pure (R)-SLB.D-DBTA (enantiomeric excess>99%, 1.404 g). The mixture was maintained at 50° C. for 30 min, then the solution was cooled to −7° C.±2° C. in 2 hours, and maintained at the temperature for 2 hours. The solid was collected by filtration and washed with cold (−5° C.) methanol (2×400 mL). Crude (R)-SLB.D-DBTA was obtained as a wet solid (1255 g, LOD=23.7% corresponding to 950 g Yield=47.5%). HPLC purity=99.5%. Optical purity: R-levalbuterol vs S-levalbuterol=95.8:4.2. The wet product was crystallized according to the procedure described in Example 6.

Example 6

Preparation of Pure (R)-SLB.D-DBTA, or (R)(−) α$^1$-[[(1,1-dimethylethyl)amino]methyl]-benzene-dimethanol.(D)-Dibenzoyltartrate In a 4 L reactor equipped with a condenser, thermometer, and mechanical stirrer at room temperature and under nitrogen, a suspension of wet (R)-SLB.(D)-DBTA (1245 g; LOD=23.7%, 950 g) in methanol (2477 mL) was formed. The suspension was heated to gentle reflux (62-63° C.) until a solution formed. The solution was cooled to 60° C., and treated with charcoal (9.5 g). After 15 min at 60-62° C. the charcoal was filtered off while the solution was maintained at 60-62° C. to avoid crystallization.

The filtrate, a clear solution, was cooled at 50° C. to obtain crystals. The solution was maintained at 50° C. for 30 min, cooled to −8° C. in 2 hours, and maintained at the temperature for 3 hours. The solid was collected by filtration and washed with cold methanol (607 mL) and ethylacetate (3×588 mL) to obtain a wet solid (1061.8 g, assay=78.4% corresponding to 832 g dry). The crystallization yield was 87.6%. The overall yield from racemic salbutamol was 41.6%. HPLC purity=99.5%; Optical purity: R-levalbuterol vs S-levalbuterol=99.88:0.12

Example 7

Preparation of Crude Levalbuterol Hydrochloride

In a 10 L reactor equipped with a condenser, thermometer, and mechanical stirrer at room temperature and under nitrogen, a suspension of pure (R)-SLB.D-DBTA (823 g, 1.378 mol), ethylacetate (9180 mL), and methanol (490 mL) was formed. The suspension was cooled to 0° C.±2° C., and HCl (37%, 161 g, 1.634 mol) was added in 30 minutes. The temperature was maintained at 0° C.±2° C. The suspension was stirred at 0° C.±2° C. for 1 hour. The solid was collected by filtration and washed with an ethylacetate:methanol mixture (95:5, 435 mL), followed by washing with ethylacetate (2×438 mL). 419.3 g of wet crude levalbuterol hydrochloride were obtained. HPLC purity=99.6%. The wet product (419.3 g) was slurried according to the procedure described in Example 8.

Example 8

Preparation of Pure Levalbuterol Hydrochloride

In a 4 L reactor equipped with a condenser, thermometer, and mechanical stirrer at 20° C. and under nitrogen, a suspension of wet crude levalbuterol hydrochloride (414.3 g), ethylacetate (2398 mL) and methanol (267 mL) was formed. The suspension was stirred at 22° C.±2° C. for 4 hours. The solid was collected by filtration and washed with an ethylacetate:methanol mixture (90:10, 533 mL), and ethylacetate (2×533 mL). The product was dried at 25° C. under vacuum (res. press. 40-45 mm Hg) for 24 hours to obtain 357.3 g (dry weight) in 93% yield from pure (R)-SLB.D-DBTA. The HPLC purity=99.87%; compound A=0.01%; compound B=0.03%; compound C=n.d. Total Unknown Impurities=0.09%; HPLC assay: 100.3%; Optical purity: R-levalbuterol vs S-levalbuterol=99.9:0.1 by HPLC; e.e.=99.8; pH=4.41; Residual solvents: EtOAc 880 ppm, MeOH 300 ppm, EtOH 65 ppm, and CH$_3$COOH 160 ppm.

Example 9

Preparation of Crude (R)-SLB.D-DBTA, or (R)(−) α$^1$-[[(1,1 Dimethylethyl)amino]methyl]-benzene-dimethanol.(D)-Dibenzoyltartrate In a 3 L reactor equipped with a condenser, thermometer, and mechanical stirrer at 20° C. and under nitrogen, salbutamol base (265 g), D-DBTA (199 g), and methanol (1190 mL) were loaded. The temperature increased from 20° C. to 35° C. The mixture was cooled to 28° C. A second portion of D-DBTA (199 g) was loaded and the suspension was heated to 60-63° C. The solution was cooled to 50° C. and seeded with pure (R)-SLB.D-DBTA (enantiomeric excess>99%, 0.46 g). The mixture was maintained at 50° C. for 30 min, cooled to −5° C. in 2 hours, and maintained at the temperature for 1.6 hours. The solid was collected by filtration and washed with cold methanol (2×139 mL).

Crude (R)-SLB.D-DBTA was obtained as a wet solid (395 g; LOD=22% corresponding to 308 g of dry product; yield=46.5%). HPLC purity=99.0%; Optical purity: R-levalbuterol vs S-levalbuterol=97.3:2.7. The wet product was crystallized according to the procedure described in Example 10.

Example 10

Preparation of Pure (R)-SLB.D-DBTA, or (R)(−) α¹-[[(1,1-dimethylethyl)amino]methyl]-benzene-dimethanol.(D)-Dibenzoyltartrate In a 2 L reactor equipped with a condenser, thermometer, and mechanical stirrer at room temperature and under nitrogen, a suspension of wet (R)-SLB.(D)-DBTA (395 g; LOD=22%, 308 g dry) in methanol (815 mL) was formed. The suspension was heated to gentle reflux (62-63° C.) until a solution formed. The solution was cooled to 60° C., and treated with charcoal (3 g). After 15 min at 60-62° C. the charcoal was filtered off while the solution was maintained at 60-62° C. to avoid crystallization.

The filtrate, a clear solution, was cooled at 50° C. to obtain crystals. The solution was maintained at 50° C. for 30 min, cooled to −8° C. in 2 hours, and maintained at the temperature for 2 hours. The solid was collected by filtration and washed with cold methanol (197 mL) and ethylacetate (3×191 mL) to obtain a wet solid (336.4 g; assay=82.3% corresponding to 277 g of dry product). The crystallization yield was 89.9%. The overall yield from racemic salbutamol was 41.8%. HPLC purity=99.0%; Optical purity: R-levalbuterol vs. S-levalbuterol=99.9:0.1.

Example 11

Preparation of Crude Levalbuterol Hydrochloride

In a 4 L reactor equipped with a condenser, thermometer, and mechanical stirrer at room temperature and under nitrogen, a suspension of pure (R)-SLB.D-DBTA (wet=331 g; assay=82,3%; 0.4559 mol), ethylacetate (3060 mL), and methanol (163 mL) was formed. The suspension was cooled to 0° C.±2° C., and HCl (37%, 53.7g, 0.545 mol) was added in 30 minutes. The temperature was maintained at 0° C.±2° C. The suspension was stirred at 0° C.±2° C. for 1 hour. The solid was collected by filtration and washed with an ethylacetate:methanol mixture (95:5, 146 mL), followed by washing with ethylacetate (2×146 mL). The wet product (137.5 g; 122 g dry) was slurried according to the procedure described in Example 12. HPLC purity=99.6%; Optical purity: R-levalbuterol vs S-levalbuterol=99.92:0.08.

Example 12

Preparation of Pure Levalbuterol Hydrochloride

In a 4 L reactor equipped with a condenser, thermometer, and mechanical stirrer at 20° C. and under nitrogen, a suspension of wet levalbuterol hydrochloride (133 g), ethylacetate (799 mL) and methanol (89 mL) was formed. The suspension was stirred at 22° C.±2° C. for 4 hours. The solid was collected by filtration and washed with an ethylacetate:methanol mixture (90:10, 178 mL), and ethylacetate (2×178 mL). The product was dried at 25° C. under vacuum (res. press. 40-45 mm Hg) for 24 hours to obtain 116 g (dry weight) in 92.3% yield from pure (R)-SLB.D-DBTA.

HPLC purity=99.91%; compound A=0.02%; compound B=0.01%; compound C=n.d.; Total Unknown Impurity=0.06%; HPLC assay: 100.3%; Optical purity: R-levalbuterol vs S-levalbuterol=99.93:0.07 by HPLC; e.e.=99.86; pH=4.86; Residual solvents: EtOAc 830 ppm; MeOH 430 ppm; EtOH 56 ppm; and $CH_3COOH$ 152 ppm.

Example 13

Preparation of Crude (R)-SLB.D-DBTA, or (R)(−) α¹-[[(1,1Dimethylethyl)amino]methyl]-benzene-dimethanol.(D)-Dibenzoyltartrate In a reactor equipped with a condenser, thermometer, and mechanical stirrer at 20° C. and under nitrogen, salbutamol base (44 Kg), D-DBTA (66 g, added in three portions), and methanol (200 L) were loaded. The temperature was kept below 32° C. The mixture was heated to 60-63° C. for 30'. The solution was cooled to 50° C. and seeded with pure (R)-SLB.D-DBTA (enantiomeric excess>99%, 0.08 Kg). The mixture was maintained at 50° C. for 30 min, cooled to −7° C.±2° C. in 2 hours and 15 minutes, and maintained at the temperature for 2 hours. The solid was collected by filtration and washed with cold (−5° C.) methanol (2×44 L). Crude (R)-SLB.D-DBTA was obtained as a wet solid (67.9 Kg, LOD=20.5% corresponding to 53.98 Kg). The wet product was crystallized according to the procedure described in Example 14.

Example 14

Preparation of Pure (R)-SLB.D-DBTA, or (R)(−) α¹-[[(1,1-dimethylethylamino]methyl]-benzene-dimethanol.(D)-Dibenzoyltartrate In a reactor equipped with a condenser, thermometer, and mechanical stirrer at room temperature and under nitrogen, a suspension of wet (R)-SLB.(D)-DBTA (67.9 Kg wet; 53.98 Kg dry) in methanol (140 L) was formed. The suspension was heated to light reflux (62-63° C.) until a solution formed. The solution was cooled to 60° C., and treated with charcoal (2 Kg) and dicalite (3 Kg). After 15 min at 60-62° C. the charcoal was filtered off while the solution was maintained at 60-62° C. to avoid crystallization; the filter was washed with hot methanol (10 L).

The filtrate, a clear solution, was cooled at 50° C. to obtain crystals. The solution was maintained at 50° C. for 30 min, cooled to −5° C. in 2.5 hours, and maintained at the temperature for 2 hours 15 min. The solid was collected by filtration and washed with cold methanol (32 L) and ethylacetate (3×100 L) to obtain a wet solid (54 Kg, assay=85.5% corresponding to 46.2 Kg dry product).

Example 15

Preparation of Crude Levalbuterol Hydrochloride

In a reactor equipped with a condenser, thermometer, and mechanical stirrer at room temperature and under nitrogen, a suspension of pure (R)-SLB.D-DBTA (45.3 Kg), ethylacetate 517 L), and methanol (22 L) was formed. The suspension was cooled to 0° C.±2° C., and HCl (37%, 9.2 Kg) was added in 30 minutes. The temperature was maintained at 0° C.±2° C. The suspension was stirred at 0° C.±2° C. for 1.5 hour. The solid was collected by filtration and washed with an ethylacetate:methanol mixture 95:5 (23 L), followed by washing with ethylacetate (2×25 L). The wet product (24.2 Kg) was slurried according to the procedure described in Example 16. HPLC purity=99.8%.

Example 16

Preparation of Pure Levalbuterol Hydrochloride

In a reactor equipped with a condenser, thermometer, and mechanical stirrer at 20° C. and under nitrogen, a suspension of wet levalbuterol hydrochloride (24.2 Kg), ethylacetate (156 L) and methanol (15 L) was formed. The suspension was stirred at 22° C.±2° C. for 4.5 hours. The solid was collected by filtration and washed with an ethylacetate:methanol mixture (90:10, 30 L), and ethylacetate (2×30 L). The product was dried at 22° C. under vacuum for 18 hours to obtain 17.9 Kg (dry weight) of pure levalbuterol hydrochloride. HPLC purity=99.86%; compound A=0.01%; compound B=0.02%; compound C=n.d.; Total Unknown Impurity=0.11%; HPLC assay: 100.3%; Optical purity: R-levalbuterol vs S-levalbuterol=99.9:0.1 by HPLC; e.e.=99.8; pH=5.30; Residual solvents: EtOAc 480 ppm; MeOH 1600 ppm; EtOH 180 ppm; and $CH_3COOH$ 170 ppm.

Example 17

Stability Comparison of Sample at 40° C. and 75% RH

Using the products of the previous examples, a stability study at 40° C. and 75% RH was carried out. Table 4 summarizes the results.

TABLE 4

Stability Comparison of Sample at 40° C. and 75% RH

| Exam. No. | Time | LVB | Comp. A | Comp. B | Comp. C | Total Unknown Impurities | MeOH (ppm) | pH |
|---|---|---|---|---|---|---|---|---|
| 8 | T = 0 | 99.87% | 0.01% | 0.03% | n.d. | 0.09% | 300 | 4.41 |
| 8 | 3 months | 99.85% | 0.03% | 0.07% | n.d. | 0.05% | — | |
| 8 | 6 months | 98.81% | 0.03% | 0.07% | n.d. | 0.09% | — | |
| 12 | T = 0 | 99.91% | 0.02% | 0.01% | n.d. | 0.06% | 430 | 4.86 |
| 12 | 3 months | 99.85% | 0.02% | 0.06% | n.d. | 0.07% | — | |
| 12 | 6 months | 99.83% | 0.02% | 0.06% | n.d. | 0.09% | — | |
| 16 | T = 0 | 99.86% | 0.01% | 0.02% | n.d. | 0.11% | 1600 | 5.30 |
| 16 | 3 months | 99.75% | 0.06% | 0.09% | 0.04% | 0.08% | — | |
| 16 | 6 months | 99.72% | 0.07 | 0.13% | 0.05% | n.d. | — | |

Example 18

Preparation of Crude (R)-SLB.D-DBTA, or (R)(−) $\alpha^1$-[[(1,1 Dimethylethyl)amino]methyl]-benzene-dimethanol.(D)-Dibenzoyltartrate In a 10 L reactor equipped with a condenser, thermometer, and mechanical stirrer at 20° C. and under nitrogen, salbutamol base (1257 g), D-DBTA (1887 g, in three portions), and methanol (5657 mL) were loaded. The temperature was kept below 32° C. The mixture was heated to 60-63° C. and a solution was obtained, which was cooled to 50° C. and seeded with pure (R)-SLB.D-DBTA (enantiomeric excess>99%, 2.2 g). The mixture was maintained at 50° C. for 30 min, cooled to −7° C.±2° C. in 2 hours, and maintained at the temperature for 2 hours. The solid was collected by filtration and washed with cold (−5° C.) methanol (2×627 mL). Crude (R)-SLB.D-DBTA was obtained as a wet solid (1879 g, LOD=19% corresponding to 1522 g dry). The wet product was crystallized according to the procedure described in Example 19. Optical purity: R-levalbuterol vs S-levalbuterol=96.9:3.1.

Example 19

Preparation of Pure (R)-SLB.D-DBTA, or (R)(−) $\alpha^1$-[[(1,1-dimethylethyl)amino]methyl]-benzene-dimethanol.(D)-Dibenzoyltartrate The solid obtained in example 18 was divided in two portions, each was treated as reported below.

In a 5 L reactor equipped with a condenser, thermometer, and mechanical stirrer at room temperature and under nitrogen, a suspension of wet (R)-SLB.(D)-DBTA (747 g) in methanol (2019 mL) was formed. The suspension was heated to gentle reflux (62-63° C.) until a solution formed. The solution was cooled to 60° C., and treated with charcoal (7.4 g). After 15 min at 60-62° C. the charcoal was filtered off while the solution was maintained at 60-62° C. to avoid crystallization. The cake was washed twice with hot methanol (77 ml).

The filtrate was cooled at 50° C. to obtain crystals. The solution was maintained at 50° C. for 30 min, cooled to −8° C. in 2 hours, and maintained at the temperature for 3 hours. The solid was collected by filtration and washed with cold methanol (478 mL) and ethylacetate (3×462 mL) to obtain a wet solid (810 g, assay=79.8% corresponding to 646 g dry). The crystallization yield was 86.5%. Optical purity: R-levalbuterol vs S-levalbuterol=99.8:0.2.

Example 20

Preparation of Crude Levalbuterol Hydrochloride

In a 10 L reactor equipped with a condenser, thermometer, and mechanical stirrer at room temperature and under nitrogen, a suspension of pure wet (R)-SLB.D-DBTA (810 g), ethylacetate (7174 mL ), and methanol (388 mL) was formed. The suspension was cooled to 0° C.±2° C., and HCl (36%, 130 g) was added in 15 minutes. The temperature was maintained at 0° C.±2° C. The suspension was stirred at 0° C.±2° C. for 1 hour. The solid was collected by filtration and washed with an ethylacetate:methanol mixture (95:5, 344 mL), followed by washing with ethylacetate (2×334 mL). The wet product (406 g) was slurried according to the procedure described in Example 21. HPLC purity=99.9%. Optical purity: R-levalbuterol vs S-levalbuterol=99.8:0.2.

Example 21

Preparation of Pure Levalbuterol Hydrochloride

In a 10 L reactor equipped with a condenser, thermometer, and mechanical stirrer at 20° C. and under nitrogen, a suspension of wet levalbuterol hydrochloride (846.7 g), ethylacetate (3810 mL) and methanol (423 mL) was formed. The suspension was stirred at 22° C.±2° C. for 4 hours. The solid was collected by filtration and washed with an ethylacetate:methanol mixture (90:10, 821 mL), and ethylacetate (2×821 mL). The product was dried at 22° C. under vacuum (res. press. 40-45 mm Hg) for 18 hours to obtain 580 g (dry weight) in 40% yield from racemic salbutamol. HPLC purity=99.82%; compound A=0.07%; compound B=0.04%; compound C=n.d.; Total Unknown Impurity=0.06.%; HPLC assay: 99%; R-levalbuterol: S-levalbuterol=99.8:0.2 by HPLC; e.e.=99.6%; pH=3.97; Residual solvents: EtOAc 870 ppm; MeOH 3420 ppm; and EtOH 490 ppm.

What is claimed is:

1. Compound B, N-(tert-butyl)-2-methoxy-2-(4-hydroxy-3-(hydroxymethyl)phen-1-yl)-ethanamine, having the following structure:

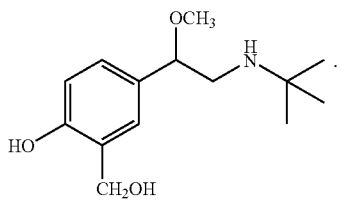

Compound B

2. Compound C, N-(tert-butyl)-2-methoxy-2-(4-hydroxy-3-(methoxy-methyl)phen-1-yl)-ethanamine, having the following structure:

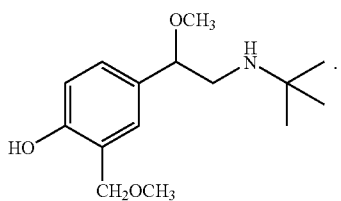

Compound C

* * * * *